US009724357B2

(12) United States Patent
Vavvas et al.

(10) Patent No.: US 9,724,357 B2
(45) Date of Patent: Aug. 8, 2017

(54) METHODS FOR PRESERVING PHOTORECEPTOR CELL VIABILITY FOLLOWING RETINAL DETACHMENT

(75) Inventors: Demetrios G. Vavvas, Boston, MA (US); Joan W. Miller, Winchester, MA (US); Dimosthenis Mantopoulos, Rahway, NJ (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 416 days.

(21) Appl. No.: 14/239,060

(22) PCT Filed: Aug. 15, 2012

(86) PCT No.: PCT/US2012/051000
§ 371 (c)(1),
(2), (4) Date: Jul. 17, 2014

(87) PCT Pub. No.: WO2013/025840
PCT Pub. Date: Feb. 21, 2013

(65) Prior Publication Data
US 2014/0323455 A1    Oct. 30, 2014

Related U.S. Application Data (60) Provisional application No. 61/523,682, filed on Aug. 15, 2011.

(51) Int. Cl.
*A61K 31/575* (2006.01)
(52) U.S. Cl.
CPC .................................. *A61K 31/575* (2013.01)
(58) Field of Classification Search
CPC .................................................. A61K 31/575
See application file for complete search history.

(56) References Cited

U.S. PATENT DOCUMENTS

| | | |
|---|---|---|
| 5,443,505 A | 8/1995 | Wong et al. |
| 5,766,242 A | 6/1998 | Wong et al. |
| 6,251,090 B1 | 6/2001 | Avery et al. |
| 6,251,884 B1 | 6/2001 | Setchell |
| 6,297,229 B1 | 10/2001 | Lindor |
| 6,299,895 B1 | 10/2001 | Hammang et al. |
| 6,375,972 B1 | 4/2002 | Guo et al. |
| 6,413,540 B1 | 7/2002 | Yaacobi |
| 6,416,777 B1 | 7/2002 | Yaacobi |
| 2004/0039253 A1* | 2/2004 | Peyman .............. A61F 9/00727 600/201 |
| 2008/0194531 A1* | 8/2008 | Steer .................... A61K 31/575 514/182 |
| 2010/0022495 A1 | 1/2010 | Hotamisligil et al. |

FOREIGN PATENT DOCUMENTS

| | | |
|---|---|---|
| WO | WO-00/40089 A1 | 7/2000 |
| WO | WO-01/028474 A1 | 4/2001 |
| WO | WO-02/089767 A1 | 11/2002 |
| WO | WO-2006/086452 A1 | 8/2006 |

OTHER PUBLICATIONS

Mantopoulos et al., "Taurorursodeoxycholic Acid (TUDCA) Protects Photoreceptors From Cell Death During Experimental Retinal Detachment," Investigative Ophthalmology & Visual Science, Meeting Abstract, Apr. 2011; 42(14): pp. 4920.*
Mantopoulos et al., "Tauroursodeoxycholic Acid (TUDCA) Protects Photoreceptors From Cell Death During Experimental Retinal Detachment." ARVO Annual Meeting Abstract, Apr. 2011, vol. 52, p. 4920.*
Ambati J et al., (2000) 'Diffusion of High Molecular Weight Compounds Through Sclera,' Invest Ophthalmol Vis Sci, 41(5):1181-5.
Ambati J et al., (2000) 'Transscleral Delivery of Bioactive Protein to the Choroid and Retina,' Invest Ophthalmol Vis Sci, 41(5):1186-91.
Arroyo JG et al., (2005) 'Photoreceptor Apoptosis in Human Retinal Detachment,' Am J Ophthalmol,139(4):605-10.
Barber AJ et al., (1998) 'Neural Apoptosis in the Retina During Experimental and Human Diabetes. Early Onset and Effect of Insulin,' J Clin Invest, 102(4):783-91.
Boatright JH et al., (2009) 'Bile Acids in Treatment of Ocular Disease,' J Ocul Biol Dis Infor, 2(3):149-59.
Campo RV et al., (1999) 'Pars Plana Vitrectomy without Scleral Buckle for Pseudophakic Retinal Detachments,' Ophthalmol, 106(9):1811-5.
Cook B et al., (1995) 'Apoptotic Photoreceptor Degeneration in Experimental Retinal Detachment,' Invest Ophthalmol Vis Sci, 36(6):990-6.
Dunaief JL et al., (2002) 'The Role of Apoptosis in Age-Related Macular Degeneration,' Arch Ophthalmol, 120(11):1435-42.
Fernández-Sánchez L et al., (2011) 'Tauroursodeoxycholic Acid Prevents Retinal Degeneration in Transgenic P23H Rats,' Invest Ophthalmol Vis Sci, 52(8):4998-5008.
Fulton AB et al., (2001) 'The Rod Photoreceptors in Retinopathy of Prematurity: An Electroretinographic Study,' Arch Ophthalmol, 119(4):499-505.
Hagimura N et al., (2002) 'Persistent Foveal Retinal Detachment After Successful Rhegmatogenous Retinal Detachment Surgery,' Am J Ophthalmol, 133(4):516-20.
Hisatomi T et al., (2001) 'Relocalization of Apoptosis-Inducing Factor in Photoreceptor Apoptosis Induced by Retinal Detachment in vivo,' Am J Pathol, 158(4):1271-8.
International Search Report for PCT/US2012/051000 mailed Jan. 31, 2013 (5 pages).

(Continued)

Primary Examiner — Sreeni Padmanabhan
Assistant Examiner — Jody Karol
(74) Attorney, Agent, or Firm — Goodwin Procter LLP (57) ABSTRACT

Provided are methods for maintaining the viability of photoreceptor cells following retinal detachment. The viability of photoreceptor cells can be preserved by administering a hydrophilic bile acid (e.g., UDCA or TUDCA) to a mammal having an eye with a detached retina. Administration of the hydrophilic bile acid maintains the viability of the photoreceptor cells until such time that the retina becomes reattached to the underlying retinal pigment epithelium and choroid, thereby minimizing the loss of vision or visual acuity, which otherwise may occur as a result of the retinal detachment.

15 Claims, 7 Drawing Sheets

(56) References Cited

OTHER PUBLICATIONS

Keene CD et al., (2001) 'A Bile Acid Protects Against Motor and Cognitive Deficits and Reduces Striatal Degeneration in the 3-Nitropropionic Acid Model of Huntington's Disease,' Exp Neurol, 171(2):351-60.

Kerr JF et al., (1972) 'Apoptosis: A Basic Biological Phenomenon with Wide-Ranging Implications in Tissue Kinetics,' Br J Cancer, 26(4):239-57.

Kroemer G et al., (2009) 'Classification of Cell Death: Recommendations of the Nomenclature Committee on Cell Death 2009,' Cell Death Differ, 16(1):3-11.

Liu H et al., (2010) 'Expression of Two Endoplasmic Reticulum Stress Markers, GRP78 and GADD153, in Rat Retinal Detachment Model and its Implications,'Eye (Lond), 24(1):137-44.

Malo A et al., (2010) 'Tauroursodeoxycholic Acid Reduces Endoplasmic Reticulum Stress, Trypsin Activation, and Acinar Cell Apoptosis while Increasing Secretion in Rat Pancreatic Acini,' Am J Physiol Gastrointest Liver Physiol, 299(4):G877-886.

Mantopoulos D (2011) 'Tauroursodeoxycholic Acid (TUDCA) Protects Photoreceptors from Cell Death after Experimental Retinal Detachment,' PLoS One, 6(9):e24245 (8 pages).

Nakazawa T et al., (2006) 'Characterization of Cytokine Responses to Retinal Detachment in Rats,' Mol Vis, 12:867-78.

Nakazawa T et al., (2007) 'Monocyte Chemoattractant Protein 1 Mediates Retinal Detachment-Induced Photoreceptor Apoptosis,' Proc Natl Acad Sci U S A, 104(7):2425-30.

Oppenheim RW, (1991) 'Cell Death During Development of the Nervous System,' Annu Rev Neurosci, 14:453-501.

Oveson BC et al., (2011) 'Constituents of Bile, Bilirubin and TUDCA, Protect Against Oxidative Stress-Induced Retinal Degeneration,' J Neurochem, 116(1):144-53.

Phillips MJ et al., (2008) 'Tauroursodeoxycholic Acid Preservation of Photoreceptor Structure and Function in the rd10 Mouse through Postnatal Day 30,' Invest Ophthalmol Vis Sci, 49(5):2148-55.

Roh MI et al., (2011) 'Edaravone, an ROS Scavenger, Ameliorates Photoreceptor Cell Death After Experimental Retinal Detachment,' Invest Ophthalmol Vis Sci, 52(6):3825-31.

Sintzel MB et al., (1996) 'Biomaterials in Ophthalmic Drug Delivery,' Eur J Pharm Biopharm, 42(6):358-74.

Trichonas G et al., (2010) 'Receptor Interacting Protein Kinases Mediate Retinal Detachment-Induced Photoreceptor Necrosis and Compensate for Inhibition of Apoptosis,' Proc Natl Acad Sci, USA, 107(50):21695-700.

Vawas D et al., (1997) 'Contraction-Induced Changes in Acetyl-CoA Carboxylase and 5'-AMP-Activated Kinase in Skeletal Muscle,' J Biol Chem, 272(20):13255-61.

Walker NI et al., (1988) 'Patterns of Cell Death,' Methods Achiev Exp Pathol, 13:18-54.

Wei H et al., (2008) 'ER and Oxidative Stresses are Common Mediators of Apoptosis in Both Neurodegenerative and Non-Neurodegenerative Lysosomal Storage Disorders and are Alleviated by Chemical Chaperones,' Hum Mol Genet, 17(4):469-77.

Written Opinion of the International Searching Authority for PCT/US2012/051000 mailed Jan. 31, 2013 (5 pages).

Wyllie AH et al., (1980) 'Cell Death: The Significance of Apoptosis,' Intl Rev Cytol, 68:251-306.

Zacks DN et al., (2003) 'Caspase Activation in an Experimental Model of Retinal Detachment,' Invest Ophthalmol Vis Sci, 44(3):1262-7.

Zacks DN et al., (2004) 'FAS-Mediated Apoptosis and Its Relation to Intrinsic Pathway Activation in an Experimental Model of Retinal Detachment,' Invest Ophthalmol Vis Sci, 45(12):4563-9.

Zhu G et al., (2000) 'Stabilization of Proteins Encapsulated in Injectable Poly(lactide-co-glycolide),' Nat Biotechnol, 18(1):52-7.

* cited by examiner

METHODS FOR PRESERVING PHOTORECEPTOR CELL VIABILITY FOLLOWING RETINAL DETACHMENT

CROSS REFERENCE TO RELATED APPLICATION

This application is the national stage of International Patent Application No. PCT/US2012/051000, filed Aug. 15, 2012, and published under PCT Article 21(2) in English, which claims the benefit of and priority to U.S. Provisional Patent Application No. 61/523,682, filed Aug. 15, 2011, the entire contents of each of which are incorporated herein by reference.

FIELD OF THE INVENTION

The field of the invention relates generally to methods for preserving the viability of photoreceptor cells following retinal detachment, and more particularly, the invention relates to methods for preserving the viability of photoreceptor cells following retinal detachment using a hydrophilic bile acid (e.g., a ursodeoxycholic acid (UDCA) or a tauroursodeoxycholic acid (TUDCA)), or pharmaceutically acceptable salt, analog, or derivative thereof.

BACKGROUND OF THE INVENTION

The retina is a delicate neural tissue lining the back of the eye that converts light stimuli into electric signals for processing by the brain. Within the eye, the retina is disposed upon underlying retinal pigment epithelium and choroid, which provide the retina with a supply of blood and nutrients. A common and potentially blinding condition known as retinal detachment occurs when the retina becomes disassociated from its underlying retinal pigment epithelium and/or choroid with the accumulation of fluid in the intervening space. The loss of visual function appears to be more pronounced when the retinal detachments involve the central macula.

Photoreceptor death after retinal detachment ("RD") is a major cause of permanent visual loss in various ocular diseases. During retinal detachment, the entire retina or a portion of the retina becomes dissociated from the underlying retinal pigment epithelium and choroid. As a result, the sensitive photoreceptor cells disposed in the detached portion of the retina become deprived of their normal supply of blood and nutrients. If untreated, the retina or, more particularly, the sensitive photoreceptor cells disposed within the retina die causing partial or even complete blindness. Physical separation of photoreceptors from the underlying retinal pigment epithelium occurs in age-related macular degeneration (Dunaief J L et al. (2002) ARCH. OPHTHALMOL. 120:1435-1442), diabetic retinopathy (Barber A J et al. (1998) J. CLIN. INVEST. 102:783-791), retinopathy of prematurity (Fulton A B et al. (2001) ARCH. OPHTHALMOL. 119:499-505), as well as rhegmatogenous (caused by a break in the retina) retinal detachment (Cook B et al. (1995) INVEST. OPHTHALMOL. VIS. SCI. 36:990-996, Arroyo J G et al. D F (2005) AM. J. OPHTHALMOL. 139:605-610). Although surgery may be carried out to reattach the retina, only two-fifths of patients with rhegmatogenous retinal detachment involving the macula, a region essential for central vision, recover 20/40 or better vision due to photoreceptor death (Arroyo et al. (2005) J. OPHTHALMOL. 139:605-610; Campo et al. (1999) OPHTHALMOLOGY 106-1811-1815). In other retinal disorders including age-related macular degeneration and diabetic retinopathy, retinal photoreceptor detachment persists chronically and vision loss progresses for many patients. Studies in humans and in experimental animal models have demonstrated that after detachment of the retina, the photoreceptors begin to degenerate and die over time. Identification of the mechanisms that underlie photoreceptor death is critical to developing new treatment strategies for these diseases.

There is still an ongoing need to minimize or eliminate photoreceptor cell death during retinal detachment. It is contemplated that minimizing photoreceptor cell death will reduce the loss of vision or the loss of visual acuity associated with retinal detachment.

SUMMARY OF THE INVENTION

The invention is based, in part, on the discovery that a hydrophilic bile acid (e.g., UDCA or TUDCA) can be used to preserve the viability of photoreceptor cells following retinal detachment. The disclosed methods comprise administering a hydrophilic bile acid or pharmaceutically acceptable salt, analog, or derivative thereof, to a subject in need thereof in an amount sufficient to preserve the viability of the photoreceptor cells disposed within the region of the detached retina. In exemplary embodiments, the hydrophilic bile acid (e.g., UDCA or TUDCA) is administered systemically (e.g., orally or parenterally).

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIGS. 1A-D provide photographs and graphs showing that TUDCA treatment decreases photoreceptor cell loss after retinal detachment.

FIGS. 2A-D provide photographs and graphs showing that TUDCA treatment does not suppress the inflammatory response associated with retinal detachment. ELISA assays were performed to determine TNF-α (FIG. 2A) and MCP-1 (FIG. 2B) levels one day after induction of retinal detachment. FIG. 2C provides immunostaining and FIG. 2D provides the quantification of infiltrating CD68+ cells (green) one day after induction of retinal detachment. Nuclei were counterstained with DAPI (blue) (n=6 for each group, $P>0.05$).

DETAILED DESCRIPTION

The invention relates to methods of preserving the viability of photoreceptor cells disposed within a retina of a mammalian eye following detachment of all or a portion of the retina. More particularly, the methods described herein comprise administering to a mammal in need of such treatment an amount of a hydrophilic bile acid (e.g., UDCA or TUDCA), or a pharmaceutically acceptable salt or analog or derivative thereof, sufficient to preserve the viability of photoreceptor cells disposed within the region of the detached retina.

Retinal detachment can occur for a variety of reasons. Although the most common reason for retinal detachment involves retinal tears, it is understood that retinal detachments can also occur because of, for example, retinoblastomas and other ocular tumors (for example, angiomas, melanomas, and lymphomas), diabetic retinopathy, retinal vascular diseases, uveitis, retinal ischemia and trauma. Furthermore, retinal detachments can occur as a result of formation of choroidal neovascularizations secondary to, for example, the neovascular form of age-related macular degeneration, pathologic myopia, and ocular histoplasmosis syndrome. It is understood that the clinical pathologies of retinal detachments are different from those of degenerative retinal disorders, for example, retinitis pigmentosa and age-related macular degeneration. However, the administration of a hydrophilic bile acid (e.g., UDCA or TUDCA) as disclosed herein may be useful in treating retinal detachments that occur secondary to an underlying degenerative retinal disorder. Accordingly, it is contemplated that the methods of the invention may be useful in minimizing or otherwise reducing photoreceptor cell death following retinal detachment, irrespective of the cause of the detachment.

It is understood that photoreceptor cell death during retinal detachments may occur as a result of either necrotic or apoptotic (also known as programmed cell death) pathways. Both of these pathways are discussed in detail in, for example, Kerr et al. (1972) BR. J. CANCER 26: 239-257, Wyllie et al. (1980) INT. REV. CYTOLOGY 68: 251-306; Walker et al. (1988) METH. ACHIE. EXP. PATROL. 13: 18-54 and Oppenheim (1991) ANN. REV. NEUROSCI. 14: 453-501. Apoptosis is a highly regulated process involving the caspase family of cysteine proteases, and is characterized by cellular shrinkage, chromatin condensation, and DNA degradation. In contrast, necrosis is associated with cellular and organelle swelling and plasma membrane rupture with ensuing release of intracellular contents and secondary inflammation (Kroemer G et al. (2009) CELL DEATH DIFFER. 16:3-11). There are a variety of assays available for determining whether cell death is occurring via a necrotic pathway or an apoptotic pathway (see, for example, Cook et al. (1995) INVEST. OPHTHALMOL. VIS. SCI. 36:990-996).

For convenience, certain terms in the specification, examples, and appended claims are collected in this section.

As used herein, the term "hydrophilic bile acid" refers to bile acids that are more hydrophilic than deoxycholic acid (DCA). This can be determined by evaluating the partition coefficient between water and octanol, with the more hydrophilic bile acids being more favorable toward water. Alternatively, the more hydrophilic bile acids have earlier retention times on a reverse-phase column using high performance liquid chromatography. Hydrophilic bile acids include ursodeoxycholic acid (UDCA), and its conjugated derivatives such as ursodeoxycholic acid 3-sulfate, ursodeoxycholic acid 7-sulfate, ursodeoxycholic acid 3,7-disulfate, tauroursodeoxycholic acid (TUDCA), and glycoursodeoxycholic acid.

One exemplary hydrophilic bile acid is UDCA or a pharmaceutically acceptable salt, analog, or derivative thereof. As used herein, "UDCA" means ursodeoxycholic acid and having the following chemical structure (I):

including pharmaceutically acceptable salts, solvates, solvates of a pharmaceutically acceptable salt, esters, polymorphs, analogs or derivatives thereof. See, for example, U.S. Pat. Nos. 6,297,229 and 6,251,884.

Another exemplary hydrophilic bile acid is TUDCA or a pharmaceutically acceptable salt, analog, or derivative thereof. As used herein, "TUDCA" means tauroursodeoxycholic acid and having the following chemical structure (II):

including pharmaceutically acceptable salts, solvates, solvates of a pharmaceutically acceptable salt, esters, polymorphs, analogs or derivatives thereof. See, for example, U.S. Patent Publication No. 2010/0022495.

As used herein, the term "cell death" is understood to mean the death of a cell by either apoptosis or necrosis.

As used herein, the term "apoptosis" is understood to mean caspase-dependent cell death, which is characterized by any of the following properties: cell shrinkage, nuclear condensation, DNA fragmentation or membrane blebbing.

As used herein, the term "necrosis" is understood to mean caspase-independent cell death characterized by any of the following properties: cellular and/or organelle swelling, plasma membrane rupture, or discontinuity in plasma, nuclear and/or organelle membranes.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "therapeutically effective amount" is understood to mean the amount of an active ingredient, for example, TUDCA, that is sufficient to reduce, minimize or eliminate the death of photoreceptor cells following retinal detachment. The compounds of the invention are administered in amounts effective at, e.g., reducing the death of photoreceptor cells following retinal detachment, preserving vision when the retina is reattached (e.g., during surgery), and/or preventing vision loss.

Disclosed herein is a method of preserving the viability of photoreceptor cells disposed within a retina of a mammalian eye following retinal detachment. The method comprises administering a hydrophilic bile acid, e.g., UDCA or TUDCA or pharmaceutically acceptable salt, analog, or derivative thereof, to the eye in which a region of the retina has been detached in amounts sufficient to preserve the viability of photoreceptor cells disposed within the region of the detached retina. The retinal detachment can be rhegmatogenous retinal detachment, tractional retinal detachment, or serious retinal detachment.

The hydrophilic bile acid, e.g., UDCA or TUDCA, may be administered in the range of from about 0.01 mg/kg to about 1500 mg/kg, optionally from about 1 mg/kg to about 1000 mg/kg, optionally from about 1 mg/kg to about 500 mg/kg, optionally from about 1 mg/kg to about 200 mg/kg, or optionally from about 5 mg/kg to about 25 mg/kg, of body weight.

In certain embodiments, the hydrophilic bile acid, e.g., UDCA or TUDCA, may be administered in an amount sufficient to give a concentration of the hydrophilic acid in the range from about 50 nM to about 10 mM, optionally from about 500 nM to about 10 mM, optionally from about 1 µM to about 10 mM, optionally from about 100 µM to about 1 mM, or optionally from about 250 µM to about 1 mM. In view of the fact that the volume of eyes in a given subject is known (for example, typical human eye contains 4 to 6 mL of fluid (humor)) it is possible to calculate the dosage of the hydrophilic bile acid to be administered to give the therapeutically effective concentrations noted herein.

In therapeutic uses for preserving the viability of photoreceptor cells disposed within a retina of a mammalian eye following retinal detachment, the hydrophilic bile acid (e.g., UDCA or TUDCA) is typically administered orally, parenterally and/or topically at a dosage to obtain and maintain a concentration that is therapeutically effective in the eye. The amount administered likely will depend on such variables as the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue-level, or the initial dosage may be smaller than the optimum and the daily dosage may be progressively increased during the course of treatment depending on the particular situation. If desired, the daily dose may also be divided into multiple doses for administration, for example, two to four times per day. For example, the hydrophilic bile acid may be administered once a day, twice a day or more frequently. In other embodiments, the hydrophilic bile acid may be administered every other day, three times a week, twice a week, or once a week.

It is contemplated that the hydrophilic bile acid (e.g., UDCA or TUDCA) may be administered before, during and/or after surgical reattachment of the detached retina. The hydrophilic bile acid may be administered to the mammal from the time the retinal detachment is detected to the time the retina is repaired, for example, via surgical reattachment. The retina may be surgically reattached using procedures known in the art. An exemplary procedure for surgically reattaching a retina following detachment includes removing the vitreous fluid and aqueous humor from the eye and applying a gas, e.g., fluoropropane, to push the retina against the choroid. Alternatively, buckle surgery, which does not require removing the vitreous fluid and aqueous humor from the eye, may be performed to reattach the retina.

It is understood, however, that under certain circumstances, it may be beneficial to administer the hydrophilic bile acid (e.g., UDCA or TUDCA) even after the retina has been surgically repaired following retinal detachment. For example, even after the surgical reattachment of a detached retina in patients with rhegmatogenous retinal detachments, persistent subretinal fluid may exist under the fovea as detected by ocular coherence tomography long after the surgery has been performed (see, Hagimura et al. (2002) AM. J. OPHTHALMOL. 133:516-520). As a result, even after surgical repair the retina may still not be completely reattached to the underlying retinal pigment epithelium and choroid. Furthermore, when retinal detachments occur secondary to another disorder, for example, the neovascular form of age-related macular degeneration and ocular melanomas, as noted above, it may be beneficial to administer the hydrophilic bile acid to the individual while the underlying disorder is being treated so as to minimize loss of photoreceptor cell viability. Accordingly, in such cases, it may be beneficial to administer the hydrophilic bile acid to the mammal for one week, two weeks, three weeks, one month, three months, six months, nine months, one year, two years or more (i) after retinal detachment has been identified, and/or (ii) after surgical reattachment of the retina has occurred, and/or (iii) after detection of an underlying degenerative disorder, so as to minimize photoreceptor cell death.

In certain embodiments, the hydrophilic bile acid (e.g., UDCA or TUDCA) may be administered following surgical reattachment of the retina or other treatments of the retina to preserve or to permit improvement of visual function. Visual function can be measured using one or more of a variety of methods well-known in the art. For example, visual function can be assessed by measuring visual acuity. Visual acuity can be assessed, for example, by using conventional "eye charts" in which visual acuity is evaluated by the ability to discern letters of a certain size, with five letters of a given size present on each line (see, e.g., the "ETDRS" eye chart described in the Murphy, R. P., CURRENT TECHNIQUES IN OPTHALMIC LASER SURGERY, $3^{rd}$ Ed., edited by L. D. Singerman, and G. Cascas, Butterworth Heinemann, 2000). Evaluation of visual acuity may also be achieved by measuring reading speed and reading time. Visual acuity may be measured to evaluate whether administration of a necrosis inhibitor and/or an apoptosis inhibitor to the affected eye preserves or permits improvement of visual acuity (e.g., to 20/40 vision or to 20/20 vision).

Visual function may also be measured by determining whether there is an increase in the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT); an improvement of the photoreceptor cell layer or its subdivisions as seen in the OCT; an improvement of visual field (e.g., by at least 10% in the mean standard deviation on the Humphrey Visual Field Test; an improvement of an electroretinograph (ERG), a measurement of the electrical response of the retina to light stimulation, (e.g., to increase ERG amplitude by at least 15%); and or preservation or improvement of multifocal ERG, which evaluates the response of the retina to multifocal stimulation and allows characterization of the function of a limited area of the retina.

Visual function may also be measured by electrooculography (EOG), which is a technique for measuring the resting potential of the retina. EOG is particularly useful for the assessment of RPE function. EOG may be used to evaluate whether administration of a necrosis inhibitor and/or an apoptosis inhibitor to the retina of the affected eye preserves or permits improvement in, for example, the Arden ratio (e.g., an increase in Arden ratio of at least 10%).

Visual function may also be assessed through fundus autofluorescence (AF) imaging, which is a clinical tool that allows evaluation of the interaction between photoreceptor cells and the RPE. For example, increased fundus AF or decreased fundus AF has been shown to occur in AMD and other ocular disorders. Fundus AF imaging may be used to evaluate whether administration of a necrosis inhibitor and/or an apoptosis inhibitor to the retina of the affected eye slows disease progression.

Visual function may also be assessed by evaluation of contrast sensitivity, which a measurement of the ability to discern between luminances of different levels in a static image. An evaluation of contrast sensitivity may be used to assess whether administration of a necrosis inhibitor and/or an apoptosis inhibitor to the retina of the affected eye preserves or permits improvement in the resolving power of the eye.

Visual function may also be assessed by microperimetry, which monitors retinal visual function against retinal thickness or structure and the condition of the subject's fixation over time. Microperimetry may be used to assess whether administration of a necrosis inhibitor and/or an apoptosis inhibitor to the retina of the affected eye preserves or permits improvement in retinal sensitivity and fixation.

In an exemplary embodiment, the hydrophilic bile acid (e.g., UDCA or TUDCA) may be administered systemically, e.g., by oral or parenteral routes. Parenteral routes include, for example, intravenous, intrarterial, intramuscular, intradermal, subcutaneous, intranasal, intraperitoneal and transdermal routes. The hydrophilic bile acid may be administered orally, in single or multiple daily doses, via pharmaceutical units such as tablets or capsules that are adapted for oral administration.

Alternatively, the hydrophilic bile acid (e.g., UDCA or TUDCA) may be administered locally to the eye, for example, by intravitreal, intraocular, intraorbital, periorbital, subconjuctival, subretinal, subtenons or transscleral routes. In an exemplary embodiment, the hydrophilic bile acid may be administered locally to the eye by intravitreal injection. In another embodiment, local administration to the eye is by topical administration, e.g., through the use of eye drops. Without wishing to be bound by theory, local modes of administration can reduce or eliminate the incidence of potential toxic side effects that may occur.

Administration may be provided as a periodic bolus (for example, intravitreally or intravenously) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag, or a contact lens slow release formulation system). The hydrophilic bile acid may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI.41:1181-1185, and Ambati et al. (2000) INVEST. OPHTHALMOL. VIS. SCI. 41:1186-1191). A variety of devices suitable for administering agents locally to the inside of the eye are known in the art. See, for example, U.S. Pat. Nos. 6,251,090, 6,299,895, 6,416,777, 6,413,540, and 6,375,972, and PCT/US00/28187.

The formulations, both for human and for veterinary medical use, typically include the hydrophilic acid in association with a pharmaceutically acceptable carrier or excipient.

The hydrophilic acid (e.g., UDCA or TUDCA) may be solubilized in a carrier, for example, a viscoelastic carrier, that is introduced locally into the eye. The hydrophilic acid also may be administered in a pharmaceutically acceptable carrier or vehicle so that administration does not otherwise adversely affect the recipient's electrolyte and/or volume balance. The carrier may comprise, for example, physiologic saline or other buffer system. In exemplary embodiments, the hydrophilic acid may be solubilized in PBS or another aqueous buffer by sonication. Alternatively, the hydrophilic acid may be solubilized using conventional solvent or solubilization systems, for example, dimethyl sulfoxide (DMSO), dimethoxyethane (DME), dimethylformamide (DMF), cyclodextran, micelles, liposomes, liposomal agents, and other solvents known in the art to aid in the solubilization and administration of hydrophobic agents.

In other embodiments, the hydrophilic acid (e.g., UDCA or TUDCA) may be solubilized in a liposome or microsphere. Methods for delivery of a drug or combination of drugs in liposomes and/or microspheres are well-known in the art.

In addition, it is contemplated that the hydrophilic acid (e.g., UDCA or TUDCA) may be formulated so as to permit release of the agent over a prolonged period of time. A release system can include a matrix of a biodegradable material or a material, which releases the incorporated agent by diffusion. The hydrophilic acid can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, under certain circumstances, synthetic release systems are preferred because generally they are more reliable, more reproducible and produce more defined release profiles. The release system material can be selected so that inhibitors having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly(lactide-co-glycolide) microsphere for intraocular injection. The microspheres are composed of a polymer of lactic acid and glycolic acid, which are structured to form hollow spheres. These spheres can be approximately 15-30 µm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for oral or parenteral administration may be in the form of discrete units such as capsules, gelatin capsules, sachets, tablets, troches, or lozenges, each containing a predetermined amount of the active agent; a powder or granular composition; a solution or a suspension in an aqueous liquid or non-aqueous liquid; or an oil-in-water emulsion or a water-in-oil emulsion. Formulations suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). Sterile injectable solutions can be prepared by incorporating the active compound in the required amount in an appropriate solvent with one or a combination of ingredients enumerated above, as required, followed by filter sterilization. Formulations suitable for intraarticular administration may be in the form of a sterile aqueous preparation of the drug which may be in microcrystalline form, for example, in the form of an aqueous microcrystalline suspension. Liposomal formulations or biodegradable polymer systems may also be used to present the drug for intraarticular administration. Formulations for topical administration to the skin surface can be prepared by dispersing the drug with a dermatologically acceptable carrier such as a lotion, cream, ointment or soap. For intranasal or inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps.

EXAMPLES

The invention is further illustrated by the following examples, which are provided for illustrative purposes only, and should not be construed as limiting the scope or content of the invention in any way.

In the examples described herein, all animal experiments adhered to the Association for Research in Vision and Ophthalmology Statement for the Use of Animals in Ophthalmic and Vision Research, and protocols were approved by the Animal Care Committee of the Massachusetts Eye and Ear Infirmary. Adult male Brown Norway rats (200 to 300 g) were purchased from Charles River Laboratories (Wilmington, Mass.). The rats were fed standard laboratory chow and allowed free access to water in an air-conditioned room with a 12 hour light/12 hour dark cycle.

Experimental retinal detachment was induced by subretinal injection of hyaluronic acid as previously described (Hisatomi T et al. (2001) AM. J. PATHOL. 158:1271-1278). Briefly, rats were anesthetized with 100 μl of a mixture of 5 parts Ketamine (100 mg/ml, Phoenix Pharmaceutical, Inc., St Joseph, Mo.), 4 parts PBS and 1 part Xylazine (100 mg/ml, Lloyd Laboratories, Inc., Shenandoah, Iowa). Body temperature was monitored and the animals were kept on a heating pad during the procedure as well as during the recovery period. The pupils were dilated with drops of phenylephrine 5%/tropicamide 0.5%. A partial retinal detachment was induced with a transscleral, subretinal injection of approximately 50 μl of 1% sodium hyaluronate (Provisc, Alcon Laboratories Inc., Fort Worth, Tex.). The partial retinal detachments occupied about 40-60% of the fundus as seen under the operating microscope. Eyes that developed choroidal hemorrhage or significant vitreous hemorrhage were excluded prior to analysis.

Animals were treated daily with an intraperitoneal injection of vehicle (0.15M $NaHCO_3$) or vehicle containing TUDCA (EMD Chemicals, Gibbstown, N.J.) at a dose that has been previously shown to be safe and effective, i.e., 500 mg/kg body weight (Keene et al. (2001) EXP NEUROL. 171: 351-360.) TUDCA was dissolved in 0.15M $NaHCO_3$ at a pH of 7.4 and at room temperature with votexing as needed.

All values disclosed below were expressed as the mean±SD. Statistical differences between two groups were analyzed by Mann-Whitney U test. Multiple group comparison was performed by ANOVA followed by Tukey-Kramer adjustments. Differences were considered significant at $P<0.05$.

Example 1

TUDCA Treatment Prevents Photoreceptor Death After Retinal Detachment

Photoreceptor death was assessed by TUNEL staining, which detects DNA fragmentation in apoptotic or necrotic nuclei. Rats were treated with either vehicle or TUDCA (500 mg/kg/day) injected intraperitoneally starting at 24 hours prior to the induction of retinal detachment. The rats were euthanized at three days or five days after induction of retinal detachment. The eyes were enucleated and fixed in 4% paraformaldehyde (PFA) in phosphate buffer saline (PBS) at 4° C. overnight. Subsequently, the eyes were embedded in Optimal Cutting Temperature media (OCT—Tissue Tek; Sakura Finetec, Torrance, Calif.), frozen at −21° C., and cut into 10 μm thick sections. The sections were fixed in 4% PFA for fifteen minutes and subjected to DAPI nuclear staining (AnaSpec/Eurogentec Group) and Terminal dUTP Nick-End Labeling (TUNEL) staining according to manufacturer's instructions (Apop Tag Fluorescein Apoptosis detection kit, Millipore, Billerica, Mass.). Fluorescence was imaged using a DM RXA microscope (Leica, Solms Germany) and digitally captured. The number of TUNEL-positive cells per $mm^2$ at the central area of the detached retina was counted in a masked fashion. All measurements were performed at ten points in each section. A total of six eyes were examined per treatment group.

Figure 1:
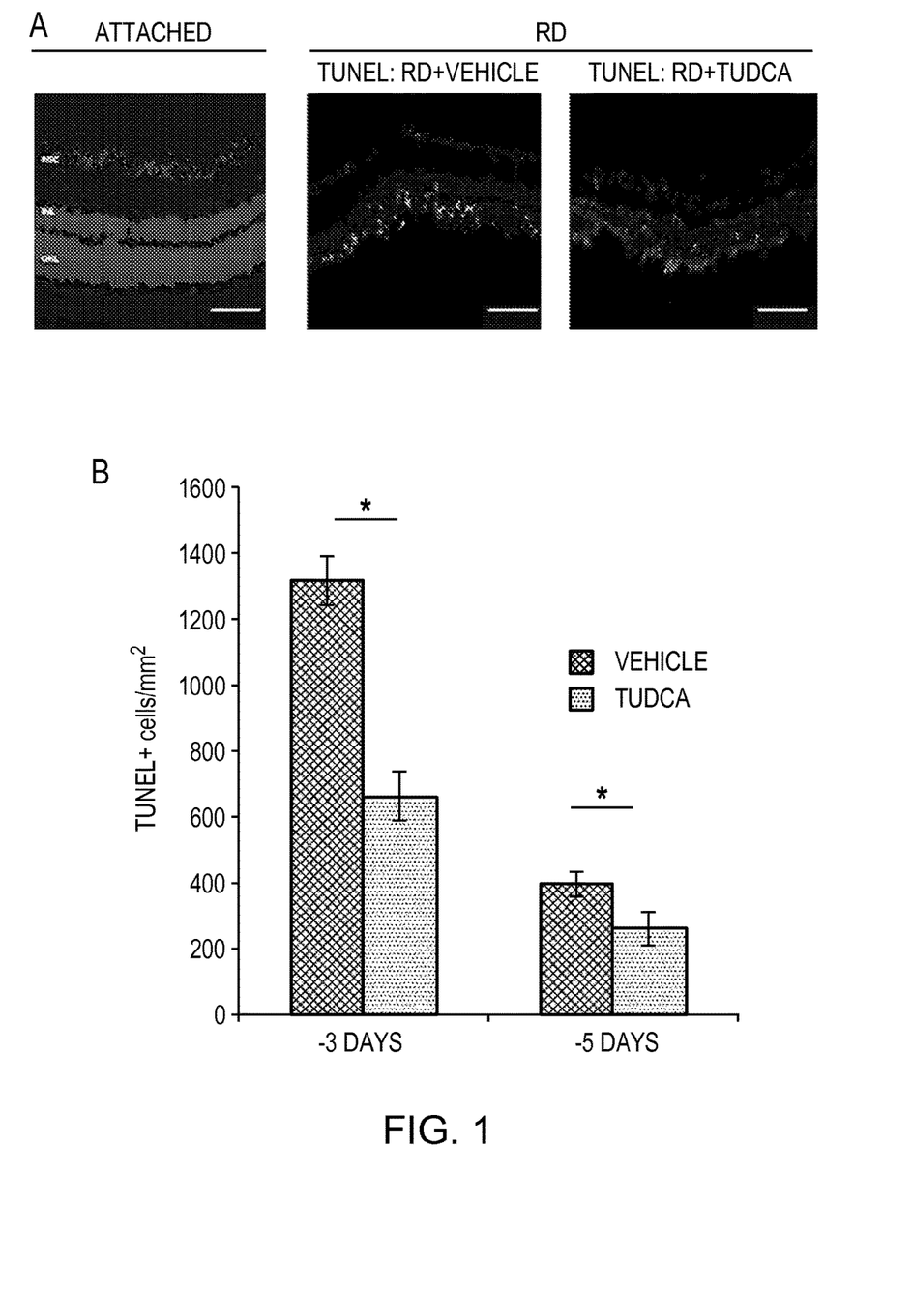
FIG. 1A shows DAPI (blue) and TUNEL (green) staining of attached or detached retina after five days of treatment with TUDCA. TUDCA treatment was started 24 hours before induction of retinal detachment and continued daily at a dose of 500 mg/kg/day.
FIG. 1B shows quantitative analysis of TUNEL positive cells at three and five days after retinal detachment with or without daily TUDCA treatment (n=6 for each group and each time point; $p<0.05$).
FIG. 1C shows the protective effect of TUDCA on ONL thickness preservation at three and five days after retinal detachment (n=6, $p<0.05$).
FIG. 1D demonstrates the protective effects of TUDCA when TUDCA treatment was started six hours after induction of retinal detachment (n=6 for each group, $P<0.05$).

Photoreceptor loss was evaluated by measuring the thickness of the outer nuclear layer (ONL). ONL thickness was determined using National Institutes of Health ImageJ software. Thickness was measured based on the outer boundaries of the DAPI nuclear stain. Because the thickness of the retina seen in cross-sections will vary depending on the angle of the sectioning plane with respect to the retina, the ONL thickness was normalized to the thickness of the entire retina. Accordingly, the data were expressed as normalized ONL thickness ratio defined as (ONL thickness/total thickness in detached retina)/(ONL thickness/total thickness in attached retina). A ratio of 1 represented no loss of ONL thickness, while a ratio of less 1 represented loss of ONL thickness. Sections just posterior to the lens were used for thickness measurements. All measurements were performed at ten points in each section. A total of six eyes were examined per treatment group. FIG. 1A shows DAPI (blue) and TUNEL (green) staining of attached or detached retina sections at five days after induction of retinal detachment.

TUDCA treatment significantly reduced the numbers of TUNEL-positive cells in outer nuclear layer (ONL) at three days after induction of retinal detachment (651±68 $mm^2$ vs. 1314±68 $mm^2$ in control group, $P=0.001$; FIG. 1B). Similar reduction in the number of TUNEL-positive cells was seen at five days after retinal detachment (243.4±23.9 $mm^2$ vs. 393.7±14.4 $mm^2$ in control group, $P=0.04$; FIG. 1B).

TUDCA treatment also reduced the loss of ONL thickness associated with retinal detachment. After three days of retinal detachment, the ONL thickness ratio of the vehicle-treated group decreased to 0.65±0.03. In comparison, the TUDCA treated group exhibited an ONL thickness ratio of 0.84±0.03, $P=0.0016$ (FIG. 1C), indicating that TUDCA prevented the loss of ONL thickness associated with retinal detachment. Five days after detachment, the ONL thickness ratio in the vehicle treated groups was 0.57±0.04 whereas in the TUDCA treated group, the ONL thickness ratio remained higher at 0.79±0.03 ($P=0.002$). Administration of TUDCA six hours after the induction of retinal detachment also showed efficient neuroprotection ($P=0.03$; FIG. 1D).

Example 2

TUDCA Treatment Does Not Affect the Inflammatory Response Associated with Retinal Detachment It has been shown previously that inflammatory cytokines and macrophage infiltration are markedly elevated in experimental retinal detachment (Nakazawa et al. (2007) PROC NATL ACAD SCI. 104: 2425-2430; Nakazawa et al. (2006) MOL VIS. 12: 867-878; Trichonas et al. (2010) PROC NATL ACAD SCI. 107(50):21695-21700). More specifically, several studies have shown upregulation of inflammatory cytokines such as TNF-α and MCP-1 and the infiltration of macrophages in the detached retina.

In order to assess macrophage infiltration in detached retinas, six eyes from each group (rats treated with vehicle or TUDCA) were analyzed. Eye sections were obtained as previously described, fixed in 4% PFA-PBS overnight, blocked in skim milk, and incubated overnight with anti-CD68 monoclonal antibody (Millipore, clone ED-1, #MAB1435). After washing with PBS, the sections were incubated with a secondary antibody Alexa Flour 488-conjugated goat anti-mouse IgG (Invitrogen, Carlsbad, Calif.) for two hours, washed, and mounted in Permafluor (Thermo Scientific, Fremont, Calif.). The number of CD68+ cells per $mm^3$ was determined using the same method as described above for the quantification of TUNEL-positive cells.

In order to measure inflammatory cytokines, eight eyes from each group (animals without retinal detachment as well as animals with retinal detachment that received vehicle or TUDCA) were analyzed using ELISA assays. Each retina was dissected and lysed in 200 µl of protein lysis buffer (Vavvas et al. (1997) J BIOL CHEM. 272: 13255-13261), sonicated for ten seconds, and centrifuged at 4° C. for five minutes at 10,000 rpm. The assays were performed on the supernatants. For the TNF-α assay (R&D Systems Inc., Minneapolis, Minn.), the samples were collected 24 hours after retinal detachment. For the MCP-1 assay (Thermo Scientific, Rockford Ill.), samples were collected at 24 and 72 hours after retinal detachment. The ELISA assays were performed according to manufacturer's instructions and the results were normalized for protein concentration in the samples using a Bio-Rad Protein Assay Kit (Bio-Rad Laboratories, Hercules, Calif. #500-0002).

Figure 2:
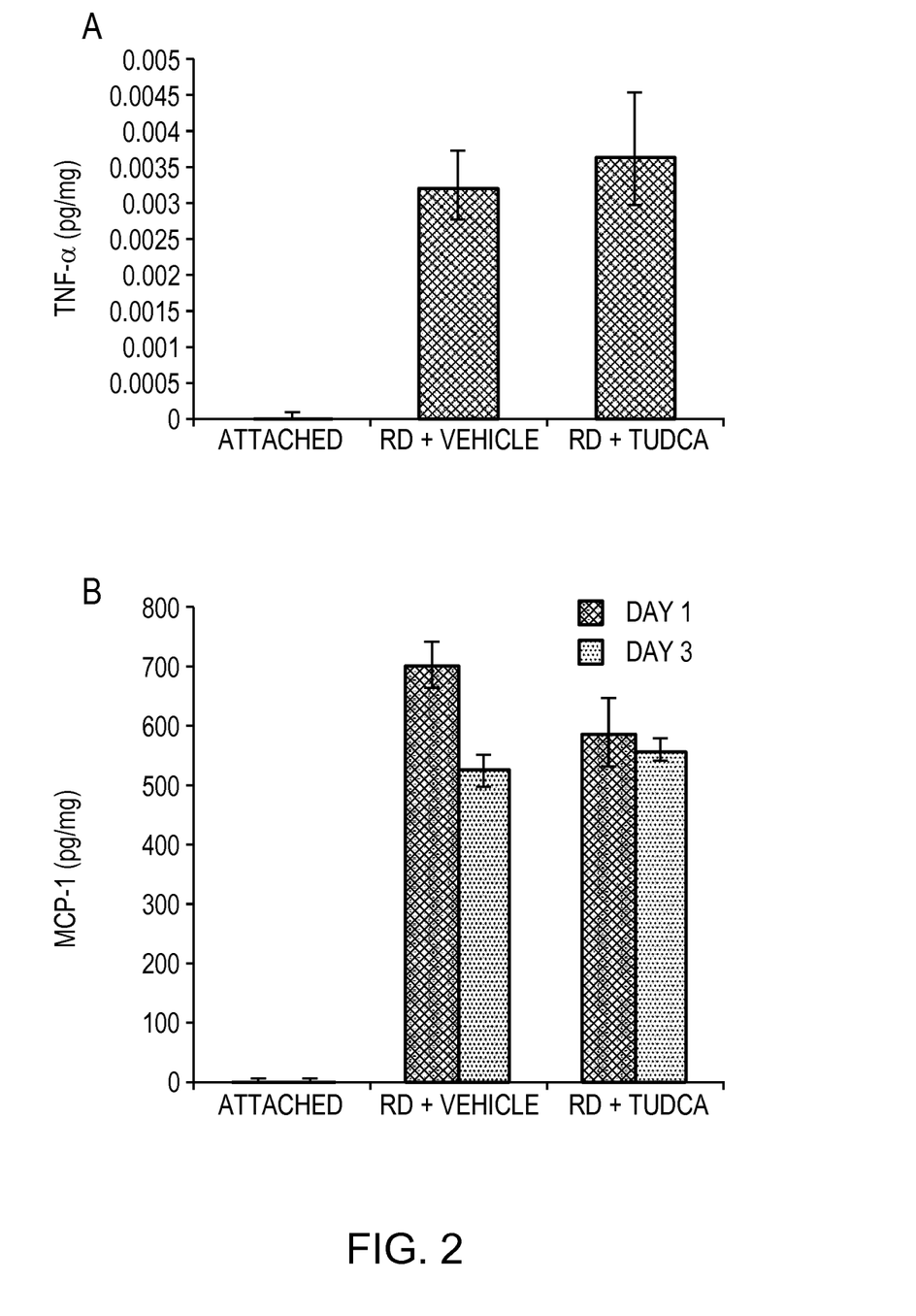

Similar to previous studies, increased levels of TNF-α, MCP-1 and CD68+ cell infiltration were noted after retinal detachment. TUDCA treatment did not affect the levels of TNF-α and MCP-1 (FIGS. 2A-B). TUDCA treatment also did not affect macrophage infiltration (FIGS. 2C-D).

Example 3

TUDCA Treatment Reduces Oxidative Stress

TUDCA has been shown to exert cytoprotective effects in different models by reducing oxidative stress (Oveson et al. (2011) J NEUROCHEM. 116: 144-153; Wei et al. (2008) HUM MOL GENET. 17: 469-477). It has also been shown previously that retinal detachment leads to increased ROS products such as increased levels of protein carbonyl content (Trichonas et al. (2010) PROC NATL ACAD SCI. 107(50):21695-21700; Roh et al. (2011) INVEST. OPHTHALMOL. VIS. SCI.).

In order to assess the effect of TUDCA treatment on oxidative stress, the protein carbonyl content in the retina was determined Eight eyes from each group (animals without retinal detachment as well as animals with retinal detachment that received vehicle or TUDCA) were analyzed using ELISA assays. Each retina was dissected and lysed in 200 µl of protein lysis buffer (Vavvas et al. (1997) J BIOL CHEM. 272: 13255-13261), sonicated for ten seconds, and centrifuged at 4° C. for five minutes at 10,000 rpm. The assays were performed on the supernatants. For measuring protein carbonyl content (Cell Biolabs, San Diego, Calif.), the samples were collected 24 hours after retinal detachment. The ELISA assays were performed according to manufacturer's instructions and the results were normalized for protein concentration in the sample using a Bio-Rad Protein Assay Kit (Bio-Rad Laboratories, Hercules, Calif. #500-0002).

Figure 3:
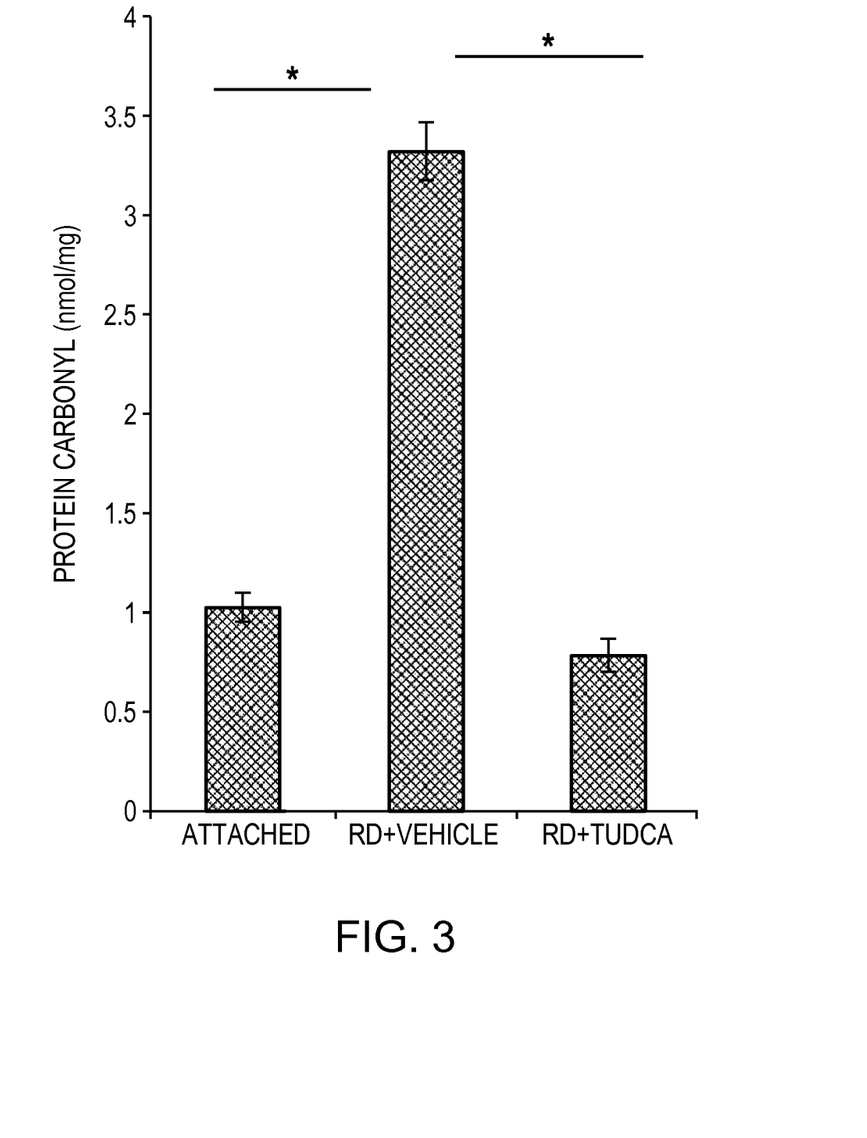
FIG. 3 provides a graph showing that TUDCA treatment suppresses oxidative stress after retinal detachment. Levels of protein carbonyl adducts were used as an index of exposure to oxidative stress. Protein carbonyl concentration increased 24 hours after induction of retinal detachment, an effect that was reversed by TUDCA treatment (n=6, p<0.05).

One day after retinal detachment, TUDCA treatment prevented an increase in protein carbonyl content after retinal detachment (FIG. 3). This data suggests that TUDCA administration reduces oxidative stress.

Example 4

TUDCA Treatment Inhibits Caspase Activation

Caspases have previously been shown to play a role in retinal detachment (Zacks et al. (2003) INVEST. OPHTHALMOL. VIS. SCI. 44: 1262-1267; Zacks et al. (2004) INVEST. OPHTHALMOL. VIS. SCI. 45: 4563-4569). The cytoprotective effects of TUDCA were investigated by measuring the activity of caspases 2, 3, 8, 9, and 11, which includes pathway members from both the intrinsic and the extrinsic apoptosis pathway.

The caspase assays were performed on the retina of animals without retinal detachment (n=6) as well as animals with retinal detachment that received vehicle (n=8) or TUDCA (n=8). The samples were stored in lysis buffer, sonicated for ten seconds, and centrifuged for five minutes at 10,000 rpm. Supernatants were retained for further analysis. For detecting the activities of caspases 2, 3, 8, and 9, a colorimetric assay was performed. This assay was based on the detection of p-nitroalanine which was released upon enzymatic cleavage of a labeled substrate DEVD-pNA from activated caspases in apoptotic cells. The assays were performed according to manufacturer's instructions (for detecting the activities of caspases 3 and 8, Casp-3-C and Casp-8-C Assay kits were used. Sigma-Aldrich, Saint Louis, Mo.; for detecting the activities of caspases 2 and 9, APT163 and APT173 Assay kits were used. Chemicon-Millipore, Temecula, Calif.). Optical density was assessed at 405 nm and normalized for protein concentration, initial optical density, and compared to a sample filled with buffer. For detection of caspase 11, western blot analysis was performed. The vitreous and neural retina was collected three days after retinal detachment. Samples were run on a 4-12% SDS-polyacrylamide gel and transferred onto PVDF membrane. After blocking with 3% nonfat dried milk, the membrane was reacted with a caspase-11 antibody (1:1000; Santa Cruz Biotechnology, Cat #SC-28230). The membrane was then developed with enhanced chemiluminescence. β-tubulin (1:1,000; Cell Signaling Technology, Cat #2146) was used as a loading control.

Figure 4:
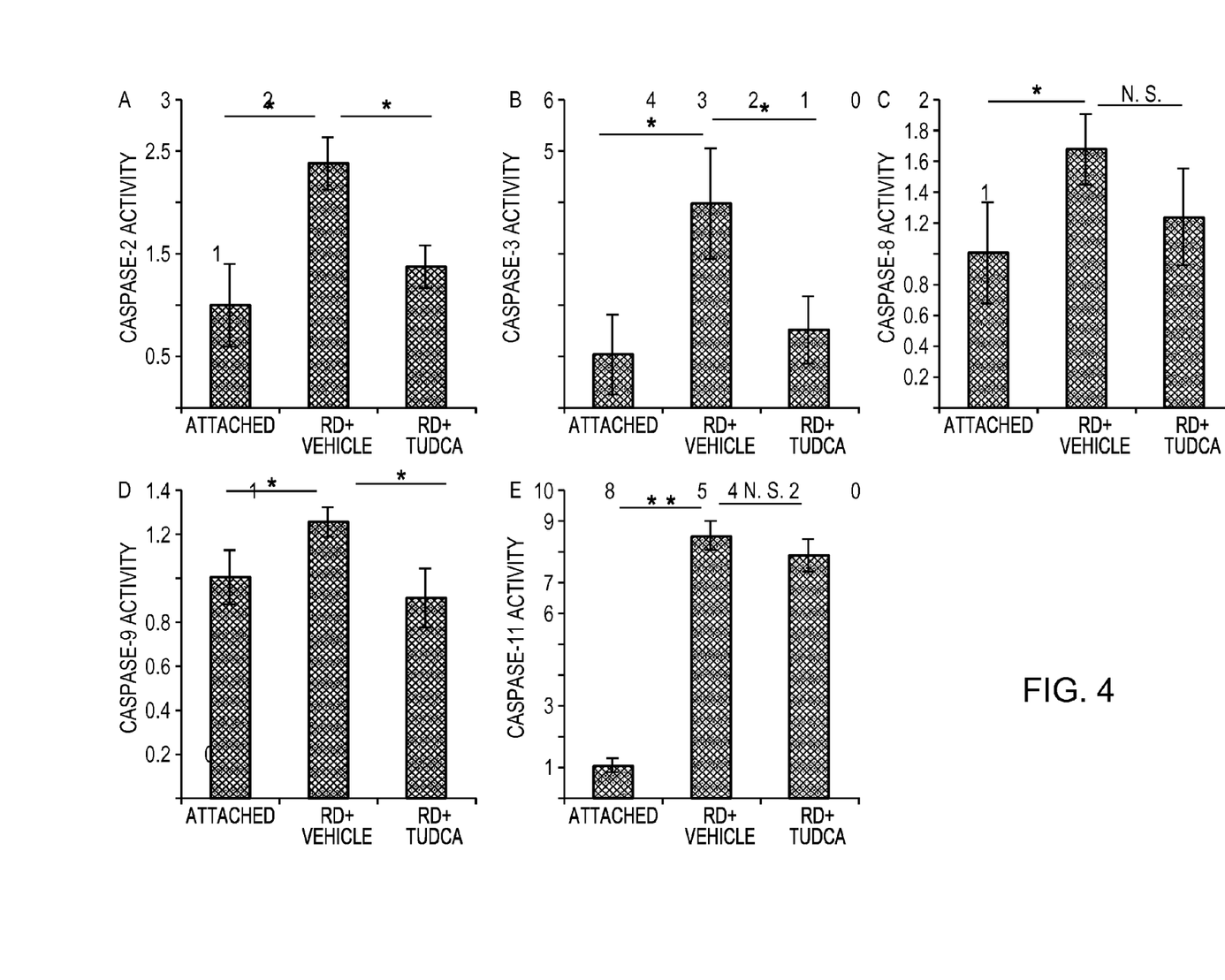
FIGS. 4A-E provide graphs showing that TUDCA treatment inhibits caspase activation after retinal detachment. Caspase activity was measured in retinal lysates 24 hours after induction of retinal detachment. TUDCA treatment decreased the activation of caspase 2 (FIG. 4A), caspase 3 (FIG. 4B) and caspase 9 (FIG. 4D) but not of caspase 8 (FIG. 4C) and caspase 11 (FIG. 4E). N=6 for each group, p>0.05.

TUDCA administration significantly decreased retinal detachment-induced activity for caspases 2, 3 and 9 (FIGS. 4A-C, respectively; P<0.05), while it did not alter the activity of caspases 8 and 11 (FIGS. 4D-E, respectively). This data suggests that TUDCA mediates its effects partially through the inhibition of caspase activity.

Example 5

TUDCA Does Not Significantly Decrease Endoplasmic Reticulum (ER) Stress After Retinal Detachment Prolonged ER stress can lead to cell death. Recently, Liu et al. (2010) EYE (Lond) 24: 137-144, have shown that proapoptotic ER stress proteins such as growth arrest DNA damage-inducible gene 153 (GADD153) also known as C/EBP homologous protein (CHOP), is increased after retinal detachment in rats. Additionally, in isolated rat pancreatic acini, TUDCA has been shown to decrease ER stress and downregulate CHOP expression (Malo et al. (2010) AM J PHYSIOL GASTROINTEST LIVER PHYSIOL. 299: G877-886). The effect of TUDCA on CHOP expression after retinal detachment was evaluated.

Western blot analysis was performed for detecting CHOP expression. The vitreous and neural retina was collected three days after retinal detachment. Samples were run on a 4-12% SDS-polyacrylamide gel and transferred onto PVDF membrane. After blocking with 3% nonfat dried milk, the membrane was reacted with a CHOP antibody (1:1000; Cell Signaling, Cat #5554S). The membrane was then developed with enhanced chemiluminescence. β-tubulin (1:1,000; Cell Signaling Technology, Cat #2146) was used as a loading control.

Figure 5:
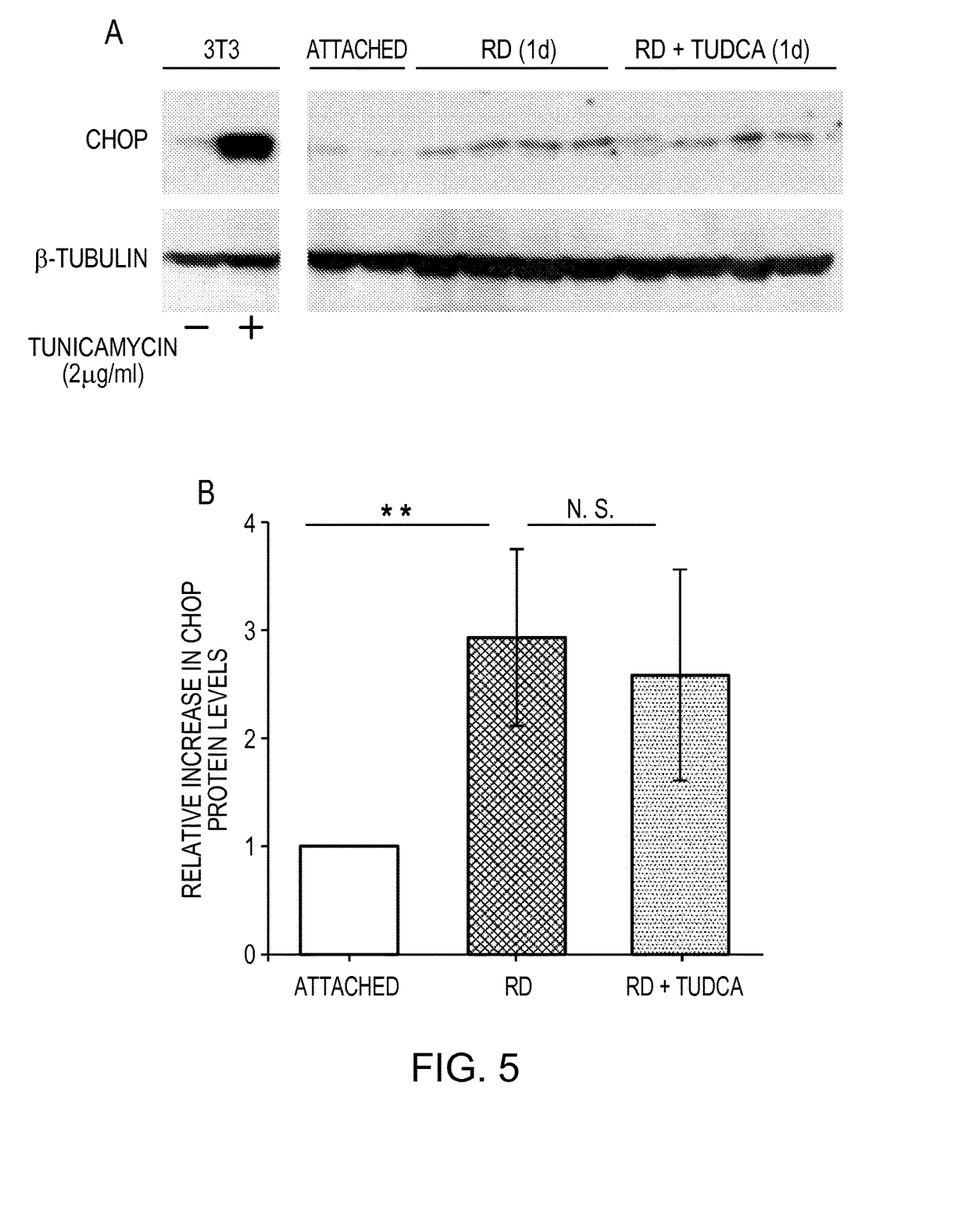
FIGS. 5A-B provide a photograph and graph showing that TUDCA treatment does not affect endoplasmic reticulum stress induced by retinal detachment. Western blot analysis (FIG. 5A) and quantification (FIG. 5B) of CHOP expression in retinal lysates from attached and detached retinas treated with TUDCA or vehicle indicate that TUDCA treatment does not alter CHOP expression (n=4, p<0.05). 3T3 fibroblasts treated with Tunicamycin (2 µg/ml for six hours) were used as a positive control.

Consistent with previous studies, retinal detachment increased the levels of CHOP. Systemic TUDCA administration, however, did not significantly alter CHOP expression (FIG. 5).

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of preserving the viability of photoreceptor cells disposed within a retina of a mammalian eye following retinal detachment, the method comprising:
administering to a mammal having an eye in which a region of the retina has been detached an amount of a hydrophilic bile acid or a pharmaceutically acceptable salt or analog thereof sufficient to preserve the viability of photoreceptor cells disposed within the region of the detached retina.

2. The method of claim 1, wherein the hydrophilic bile acid is a ursodeoxycholic acid (UDCA).

3. The method of claim 1, wherein the hydrophilic bile acid is a tauroursodeoxycholic acid (TUDCA).

4. The method of claim 1, wherein from about 1 mg/kg to about 1,000 mg/kg of the hydrophilic bile acid or a pharmaceutically acceptable salt or analog thereof is administered.

5. The method of claim 1, wherein from about 1 mg/kg to about 500 mg/kg of the hydrophilic bile acid or a pharmaceutically acceptable salt or analog thereof is administered.

6. The method of claim 1, wherein from about 1 mg/kg to about 200 mg/kg of the hydrophilic bile acid or a pharmaceutically acceptable salt or analog thereof is administered.

7. The method of claim 1, wherein from about 5 mg/kg to about 25 mg/kg of the hydrophilic bile acid or a pharmaceutically acceptable salt or analog thereof is administered.

8. The method of claim 1, wherein from about 50 nM to about 10 mM of the hydrophilic bile acid or a pharmaceutically acceptable salt or analog thereof is administered.

9. The method of claim 1, wherein the hydrophilic bile acid or the pharmaceutically acceptable salt or analog thereof is administered to the mammal prior to reattachment of the region of detached retina.

10. The method of claim 1, wherein the hydrophilic bile acid or the pharmaceutically acceptable salt or analog thereof is administered to the mammal after reattachment of the region of detached retina.

11. The method of claim 1, wherein the hydrophilic bile acid or the pharmaceutically acceptable salt or analog thereof is administered locally to the eye.

12. The method of claim 1, wherein the hydrophilic bile acid or the pharmaceutically acceptable salt or analog thereof is administered by intraocular, intravitreal, or transcleral administration.

13. The method of claim 1, wherein the hydrophilic bile acid or the pharmaceutically acceptable salt or analog thereof is administered systemically.

14. The method of claim 13, wherein the hydrophilic bile acid or the pharmaceutically acceptable salt or analog thereof is administered parenterally or orally.

15. The method of claim 1, wherein the retinal detachment occurs as a result of a retinal tear, retinoblastoma, melanoma, diabetic retinopathy, uveitis, choroidal neovascularization, retinal ischemia, pathologic myopia, or trauma.

* * * * *